United States Patent [19]

Lehmer

[11] Patent Number: 5,135,530

[45] Date of Patent: Aug. 4, 1992

[54] ANTERIOR CAPSULAR PUNCH WITH DEFORMABLE CUTTING MEMBER

[76] Inventor: Lara Lehmer, 3301 S. Sepulveda Blvd., No. 13, Los Angeles, Calif. 90034

[21] Appl. No.: 790,549

[22] Filed: Nov. 12, 1991

[51] Int. Cl.$^5$ .......................... A61F 9/00; A61B 17/32
[52] U.S. Cl. .................................... 606/107; 606/166; 606/167; 128/898
[58] Field of Search ............... 623/5, 6; 606/107, 113, 606/159, 161, 166, 167, 170, 184; 128/898

[56] References Cited

U.S. PATENT DOCUMENTS

| | | | |
|---|---|---|---|
| 4,766,897 | 8/1988 | Smirmaul | 128/305 |
| 4,785,810 | 11/1988 | Baccala et al. | 128/321 |
| 4,844,065 | 7/1989 | Faulkner | 128/321 |
| 4,959,070 | 9/1990 | McDonald | 623/6 |

FOREIGN PATENT DOCUMENTS

| | | | |
|---|---|---|---|
| 242673 | 2/1987 | Fed. Rep. of Germany | 606/166 |
| 2588751 | 4/1987 | France | 606/166 |
| 1360728 | 12/1987 | U.S.S.R. | 606/107 |
| 1431752 | 10/1988 | U.S.S.R. | 606/107 |

*Primary Examiner*—Randall L. Green
*Assistant Examiner*—Mary Beth O. Jones
*Attorney, Agent, or Firm*—Thomas I. Rozsa

[57] ABSTRACT

The present invention is an anterior capsular incising apparatus having a pair of crisscrossing arms hinged at a crisscross joint and each having a forward portion and a rearward portion and a deformable circular cutting ring having a sharp bottom circular cutting edge detachably mounted onto and between the forward portions of the pair of crisscross arms, such that the deformable circular cutting ring can be compressed into a narrow elliptical shape by squeezing the rearward portions of the pair of crisscrossing arms. The present invention anterior capsular incising method utilizes the deformable circular cutting ring in cataract surgery and includes compressing the deformable circular cutting ring into a narrow elliptical shape, inserting it into the anterior chamber of an eye through a narrow wound cut on the corneoscleral tissue of the eye, allowing it to fully return to its original configuration once inside the anterior chamber, cutting an incision on the anterior lens capsule of the eye, compressing it into the narrow elliptical shape again, and withdrawing it from the anterior chamber through the narrow wound on the corneoscleral tissue.

24 Claims, 3 Drawing Sheets

ANTERIOR CAPSULAR PUNCH WITH DEFORMABLE CUTTING MEMBER

BACKGROUND OF THE INVENTION

1. Field of the Invention

The present invention relates to the field of apparatus for ophthalmic surgery. More particularly, the present invention relates to the field of apparatus for cataract surgery.

2. Description of the Prior Art

In many types of ophthalmic surgery, it is often necessary to incise the anterior lens capsule of the crystalline lens of an eye to provide an opening on the anterior lens capsule so that the cataractous opaque lens can be removed. However, the anterior lens capsule of the eye is shielded by the corneal tissue. Therefore, before any cataract surgical apparatus can reach the anterior lens capsule of the eye, a passage wound has to be cut in the corneal tissue. After the cataract surgery, the corneal wound is closed with sutures.

The following prior art patents are found to be related to the field of surgical apparatus used in cataract surgeries.

1. U.S. Pat. No. 4,959,070 issued to McDonald on Sep. 25, 1990 for "Intraocular Lens Implantation" (hereafter referred to as the "McDonald Patent").
2. U.S. Pat. No. 4,844,065 issued to Faulkner on Jul. 4, 1989 for "Intraocular Lens Inserting Tool And Methods" (hereafter referred to as the "Faulkner Patent").
3. U.S. Pat. No. 4,785,810 issued to Baccala et al. on Nov. 22, 1988 for "Intraocular Lens Folding And Insertion Apparatus" (hereafter referred to as the "Baccala Patent").
4. U.S. Pat. No. 4,766,897 issued to Smirmaul on Aug. 30, 1988 for "Cataract Surgical Instrument" (hereafter referred to as the "Smirmaul Patent").

The Smirmaul Patent discloses an anterior lens capsule incising apparatus 10 for cutting an incision on the anterior capsule of the crystalline lens of an eye. The Smirmaul Patent incising apparatus 10 has a forward portion and a rearward portion interconnected by an elongated hollow shank 16, where the forward portion includes a circular blade holder 18, and the rearward portion includes a squeezable handle 12. There is a circular cutting blade 20 rotatably mounted within the circular blade holder 18 and attached to an elongated flexible wire 24, which in turn is disposed in the elongated hollow shank 16 and connected to the squeezable handle 12. When the handle 12 is squeezed, the flexible wire 24 will be stretched, which in turn will rotate the circular cutting blade 20. During cataract surgery, the forward portion of the incising instrument 10 is inserted through a passage wound cut on the corneal tissue of an eye, such that the circular blade holder 18 is disposed above the anterior lens capsule of the eye. When the handle 12 is squeezed, the rotatable cutting blade 20 cuts a circular incision on the anterior lens capsule of the eye for further intraocular surgery.

The Baccala Patent discloses an intraocular lens implanting apparatus 10 for inserting an artificial intraocular lens into the lens capsule of an eye, after an incision is cut on the anterior lens capsule and the natural intraocular lens is removed. The Baccala Patent implanting apparatus 10 has two elongated forceps arms 34 and 42. The front tip 16 of the first elongated forceps arm 34 has a concave surface 20, and the front tip 18 of the second elongated forceps arm 42 has a convex surface 22. An artificial intraocular lens can be folded between the concave surface 20 of the front tip 16 of the first elongated forceps arm 34 and the convex surface 22 of the front tip 18 of the second elongated forceps arm 42, and introduced into the lens capsule of an eye through the incision on the anterior lens capsule of the eye.

The Faulkner Patent also discloses an intraocular lens implanting apparatus 10. The Faulkner Patent implanting apparatus 10 has two elongated forceps arms 11 and 12. The front tips of the two elongated forceps arms 11 and 12 form jaws 13 for folding and holding an artificial intraocular lens. As shown in FIG. 8, when the jaws 13 are opened in the anterior chamber of an eye to release the artificial intraocular lens, the bent portion 27 of the two elongated forceps arms 11 and 12 are opened accordingly. Since the bent portion 27 is located within the wound cut on the corneal tissue, a relatively wide wound is required for allowing the bent portion 27 to expand.

The McDonald Patent again discloses an intraocular lens implanting apparatus 21. The McDonald Patent implanting apparatus 21 has two elongated forceps arms 22a and 23a crossing over each other and hingeably attached at point 24. When the front tips 22c and 23c are opened inside the anterior chamber, the hinge point 24 is located at the wound cut on the corneal tissue. Since the width of the hinge point 24 is fixed, the wound on the corneal tissue can be relatively narrow.

In the above four prior art patents, three of them, the Baccala Patent, the Faulkner Patent and the McDonald Patent, are not anterior lens capsule incising apparatus, but rather intraocular lens implanting apparatus. An anterior lens capsule incising apparatus is used in cataract surgery for cutting an incision on the anterior lens capsule of an eye, so that the natural lens of the eye can be removed and an artificial intraocular lens can be implanted therein. Alternatively, an intraocular lens implanting apparatus is used in the cataract surgery for inserting the artificial intraocular lens into the lens capsule of the eye, after the incision is cut on the anterior lens capsule of the eye and the natural intraocular lens of the eye is removed. The Baccala Patent, the Faulkner Patent and the McDonald Patent apparatus are more like a forceps apparatus, and none of them contain cutting blades for performing the function of cutting the incision on the anterior lens capsule of the eye.

The Smirmaul Patent apparatus 10 is an anterior lens capsule incising apparatus. Its forward portion, including the circular lens holder 18, can be inserted through a passage wound cut on the corneoscleral tissue of an eye, and disposed above the anterior lens capsule of the eye, so that its rotatable cutting blade 20 can cut a circular incision on the anterior lens capsule. The disadvantage of the Smirmaul Patent incising apparatus 10 is that it requires a wide passage wound cut on the corneoscleral tissue. The diameter of the rotatable circular cutting blade 20 of the Smirmaul Patent incising apparatus 10 is about six millimeters (6mm) (Column 3, line 23), which is the necessary size for cutting an adequate incision on the anterior lens capsule for further surgeries. Therefore the overall diameter of the circular blade holder is at least above seven millimeters (7mm). This requires that the width of the passage wound cut on the corneoscleral tissue to be not less than seven millimeters (7mm), which is wide by eye surgery standards. It is desirable to have the width of the passage wound cut on the corneoscleral tissue as narrow as possible, since a wider wound requires more surgical closing procedures and increases the period of convalescence.

Therefore, it is desirable to have an anterior lens capsule incising apparatus which can cut an adequate sized incision on the anterior lens capsule of an eye, but can also pass through a relatively narrow wound cut on the corneoscleral tissue of the eye.

SUMMARY OF THE INVENTION

The present invention is an apparatus as well as a method used in cataract surgery for cutting an adequate sized incision on the anterior lens capsule of an eye, so that the natural intraocular lens of the eye can be removed, and an artificial intraocular lens can be implanted.

It is an object of the present invention to provide an anterior lens capsule incising apparatus, which is able to cut an adequate sized incision on the anterior lens capsule of an eye. For the surgical purposes of removing the natural intraocular lens of the eye and implanting a correctly sized artificial intraocular lens, it is preferable for the incision on the anterior lens capsule to be a circular incision having a diameter of about five millimeters (5mm) or more. Hence, a preferable anterior lens capsule incising apparatus should have a circular blade having a diameter of not less than five millimeters (5mm).

It is also an object of the present invention to provide an anterior lens capsule incising apparatus, which requires only a very narrow wound cut on the corneoscleral tissue. It is desirable to limit the width of corneoscleral tissue wound to not more than four millimeters (4mm). Hence the preferable anterior lens capsule incising apparatus should be able to pass through a narrow corneoscleral tissue wound having a width of not more than four millimeters (4mm).

Therefore, the preferable anterior lens capsule incising apparatus should have a circular cutting blade having a diameter of not less than five millimeters (5mm). Additionally, the preferable anterior lens capsule incising apparatus should be able to pass through a narrow corneoscleral tissue wound having a width of not more than four millimeters (4mm). These two requirements present a challenge to the design and construction of the anterior lens capsule incising apparatus used in cataract surgery.

The present invention solves this problem by utilizing a unique deformable circular cutting ring. The diameter of the unique deformable circular cutting ring is not less than five millimeters (5mm), so that it can cut an adequate sized incision on the anterior lens capsule of an eye. The unique deformable circular cutting ring is provided between the two forward portions of two elongated arms. The two elongated arms crisscross each other and are hinged together at the crisscross joint. The rearward portion of the two arms are spring biased to keep the forward portion of the two arms spaced apart, such that the deformable circular cutting ring is in its original circular shape. When the rearward portions of the two arms are squeezed toward each other, the forward portions of the two arms will move toward each other to compress the deformable circular cutting ring into a narrow elliptical shape. The overall width of the narrow elliptical shaped deformable circular cutting ring and the forward portions of the two elongated arms become less than four millimeters (4mm), so that the narrow elliptical shaped deformed cutting ring and the forward portions of the two elongated arms can be inserted into the anterior chamber of the eye through a narrow corneoscleral tissue wound of about four millimeters (4mm) in width. The crisscross joint of the two elongated arms is located at or adjacent to the corneoscleral tissue wound. Once inside the anterior chamber of the eye, the rearward portions of the two arms are released, so that the forward portions of the two arms can move away from each other to allow the deformable circular cutting ring return to its original circular shape. Then the full size circular cutting ring is pressed onto the anterior lens capsule to cut an adequate sized circular incision, so the natural intraocular lens of the eye can be removed, and an artificial intraocular lens can be implanted therein. The deformable circular cutting ring is taken out of the anterior chamber through the narrow wound on the corneoscleral tissue by again compressing it into a narrow elliptical shape.

It is therefore an object of the present invention to provide a deformable cutting ring to the anterior lens capsule incising apparatus, where the deformable cutting ring is supported between the forward portions of two elongated crisscrossing arms, so that it can be compressed into a narrow elliptical shape by squeezing the rearward portions of the two elongated crisscrossing arms for passing through a narrow wound cut on the corneoscleral tissue of an eye.

It is another object of the present invention to provide a locking mechanism to the anterior lens capsule incising apparatus for preventing the deformable cutting ring from rotating about its axis, so that the cataract surgeon can control the exact orientation of the deformable cutting ring and the cutting edge of the deformable cutting ring is evenly applied on the anterior lens capsule.

It is also an object of the present invention to provide a biasing mechanism to the anterior lens capsule incising apparatus for keeping the two elongated crisscrossing arms in a balanced position, so that when the rearward portions of the two elongated crisscrossing arms are not squeezed, the deformable cutting ring supported by and disposed between the forward portions of the two elongated crisscrossing arms is neither compressed nor stretched.

It is a further object of the present invention to provide a mounting mechanism to the anterior lens capsule incising apparatus for detachably mounting the deformable cutting ring onto the forward portions of the two elongated arms, so that after being used for one patient, the deformable circular cutting ring can be detached from the forward portions of the two elongated arms to be sharpened, sterilized or disposed of.

It is an even further object of the present invention to provide an anterior capsular incising method utilizing the deformable circular cutting ring being supported by and disposed between the forward portions of two elongated crisscrossing arms, and being compressible and controllable when squeezing the rearward portions of the two elongated crisscrossing arms.

It is understood that the numerical values given here, e.g., four millimeters (4mm) and five millimeters (5mm), are provided for illustrative purposes and are typical only for normal situations in cataract surgery. Under other circumstances, different numerical values of the diameter of an anterior capsular incision and the width of the corneoscleral tissue wound may apply, and the present invention anterior capsular incising apparatus can also be adapted to those different sizes.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 8, FIG. 9, FIG. 10 and FIG. 11 illustrate the present invention method of using the present invention anterior capsular incising apparatus for cutting an adequate sized anterior capsular incision through a narrow corneoscleral tissue wound.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIGS. 1 through 4, there is shown at 100 the present invention anterior capsular incising apparatus. The present invention anterior capsular incising apparatus 100 has a first elongated arm 110 and a second elongated arm 120. The first elongated arm 110 has a front end 112, a rear end 114, a clamp portion 116 close to the front end 112 and a handle portion 118 close to the rear end 114. The second elongated arm 120 also has a front end 122, a rear end 124, a clamp portion 126 close to the front end 122 and a handle portion 128 close to the rear end 124. The first and second elongated arms 110 and 120 are hingeably attached together at a crisscross joint 102 by a small roll pin 104 in a crisscrossing fashion. The handle portions 118 and 128 of the first and second elongated arms 110 and 120 may be curved and widened and have serrated outer surfaces 111 and 121 respectively for easy handling. In addition, when hingeably attached in the crisscross fashion, the clamp portion 116 of the first elongated arm 110 and the clamp portion 126 of the second elongated arm 120 are disposed in a horizontal plane, and the handle portion 118 of the first elongated arm 110 and the handle portion 128 of the second elongated arm 120 are disposed in an incline plane. The incline angle $\beta$ may be 30° or other suitable degrees. Moreover, there may be an optional stopper strut 106 attached to the inner side of the handle portion of one of the two elongated arms. The optional stopper strut 106 may be integrally formed with the handle portion of the particular one of the two elongated arms.

The novel member of the present invention anterior capsular incising apparatus 100 is a deformable circular cutting ring 130. The circular cutting ring 130 is a very thin and narrow circular member. Its original configuration is preferably a perfect circle. However, the circular cutting ring 130 is deformable, which means when it is compressed at two spaced apart locations such as the two ends of a diameter, it will deform into a narrow configuration such as an ellipse. Furthermore, the deformable circular cutting ring 130 has a very sharp bottom circular cutting edge 132, so when it is pressed down onto the anterior lens capsule of an eye, the sharp bottom edge 132 can cut a circular incision on the anterior lens capsule.

Figure 1:
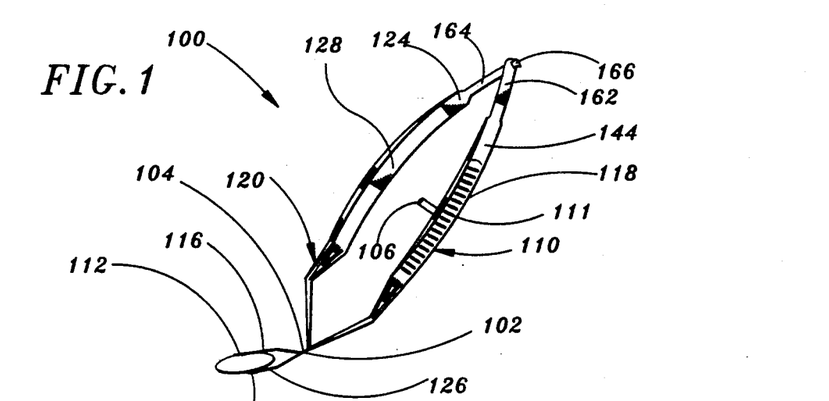
FIG. 1 is a perspective view of the present invention anterior capsular incising apparatus.
Figures 2, 3:
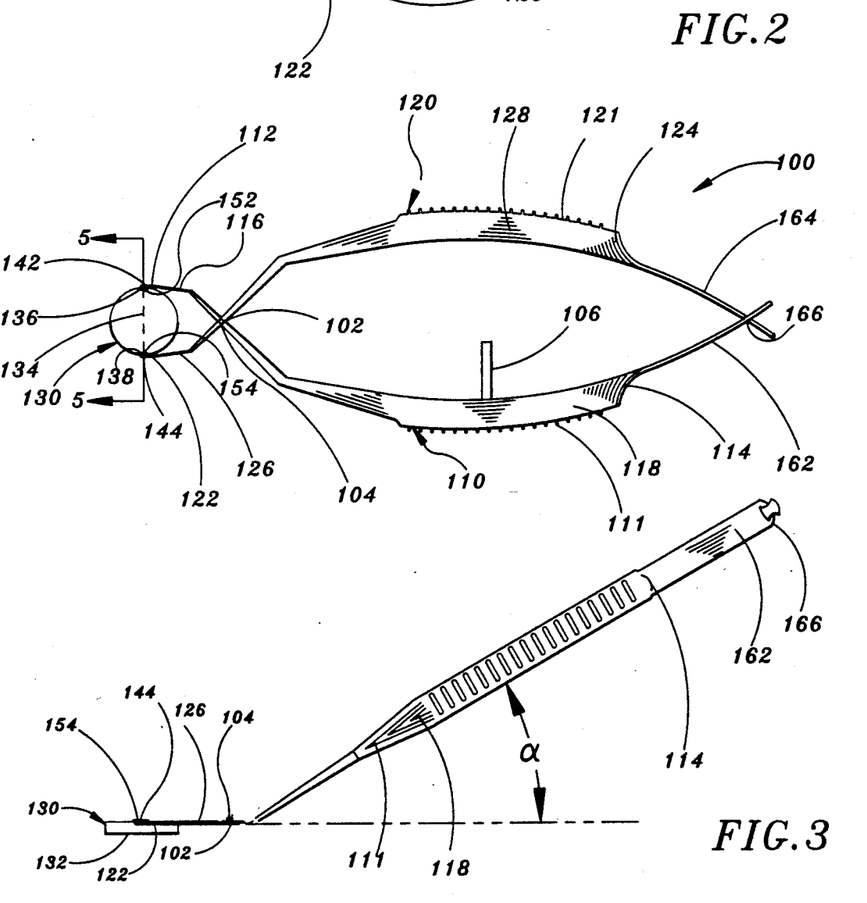
FIG. 2 is a top plan view of the present invention anterior capsular incising apparatus.
FIG. 3 is a side elevational side view of the present invention anterior capsular incising apparatus.
Figures 4, 5, 6, 10:
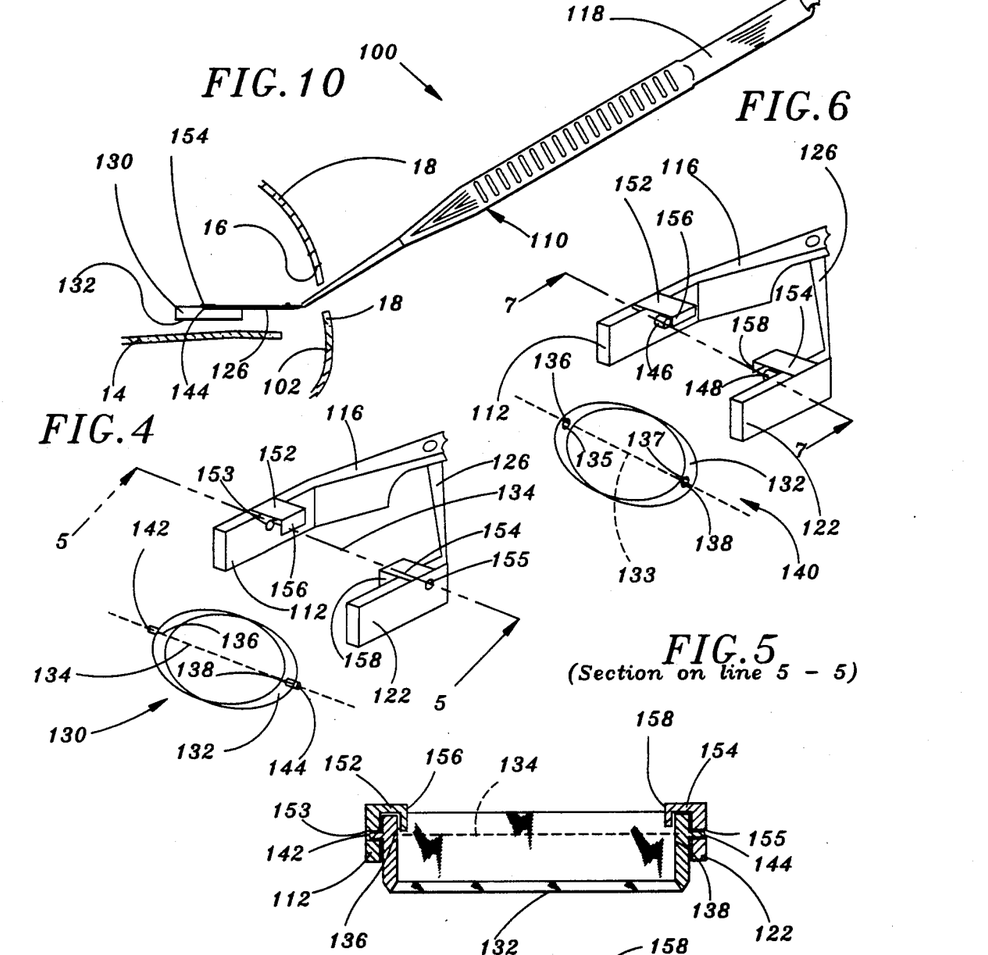
FIG. 4 is an enlarged partial view of the forward part of the present invention anterior capsular incising apparatus showing one of the preferred embodiments of the attachment assembly of the circular cutting ring, with the cutting ring removed.
FIG. 5 is a cross-sectional view taken along line 513 5 of FIG. 4.
FIG. 6 is an enlarged partial view of the forward part of the present invention anterior capsular incising apparatus showing an alternative embodiment of the attachment assembly of the circular cutting ring, with the cutting ring removed.
FIG. 10 is a side elevational view showing the crisscross joint of the present invention anterior capsular incising apparatus is located at the narrow corneoscleral wound when the forward portion of the present invention anterior capsular incising apparatus is pressed down to cut the anterior capsular incision.
Figure 7:
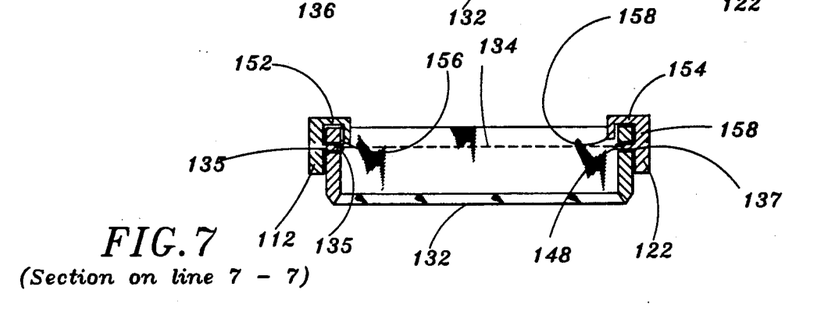
FIG. 7 is a cross-sectional view taken along line 7—7 of FIG. 6.

The deformable circular cutting ring 130 is detachably mounted onto the front ends 112 and 122 of the first and second elongated arms 110 and 120, such that it is disposed between the two clamp portions 116 and 126 of the first and second elongated arms 110 and 120. Preferably the front ends 112 and 122 of the first and second elongated arms 110 and 120 are aligned with a diameter 134 of the deformable circular cutting ring 130, i.e., the deformable circular cutting ring 130 is mounted on the front ends 112 and 122 of the first and second elongated arms 110 and 120 at the two opposite ends 136 and 138 of the diameter 134. The two opposite ends 136 and 138 of the diameter 134 of the deformable circular cutting ring 130 may be detachably mounted to the front ends 112 and 122 of the first and second elongated arms 110 and 120 respectively by a detachable mounting mechanism. The detailed assemblies of the detachable mounting mechanism are shown in FIGS. 4 through 7. One embodiment is shown in FIGS. 4 and 5, and an alternative embodiment is shown in FIGS. 6 and 7.

The assemblies of the detachable mounting mechanism shown in FIGS. 4 and 5 includes two small pegs 142 and 144 integrally mounted on the deformable circular cutting ring 130 at the two opposite ends 136 and 138 of the diameter 134, and two small holes 153 and 155 located on the front ends 112 and 122 of the first and second elongated arms 110 and 120. When the deformable circular cutting ring 130 is mounted onto the front ends 112 and 122 of the first and second elongated arms 110 and 120, the two pegs 142 and 144 are inserted and retained in the two holes 153 and 155 respectively. The assemblies of the detachable mounting mechanism further includes two small flanges 152 and 154 attached on the front ends 112 and 122 of the first and second elongated arms 110 and 120 respectively, for preventing the deformable circular cutting ring 130 from rotating about the diameter 134, so that the cataract surgeon can control the exact orientation of the deformable circular cutting ring 130, and the sharp bottom circular cutting edge 132 of the deformable circular cutting ring 130 is evenly applied on the anterior lens capsule for cutting a circular incision. In addition, the small flange 152 has a folded portion 156, and the small flange 154 has a folded portion 158, for preventing the deformable circular cutting ring 130 from staying compressed, so that the spring mechanism of the handle can pull it open if necessary.

Alternatively, the assemblies of the detachable mounting mechanism shown in FIGS. 6 and 7 includes two small pegs 146 and 148 integrally mounted on the front ends 112 and 122 of the first and second elongated arms 110 and 120, and two small holes 135 and 137 located at the deformable circular cutting ring 140 at the two opposite ends 136 and 138 of the diameter 134. When the deformable circular cutting ring 140 is mounted onto the front ends 112 and 122 of the first and second elongated arms 110 and 120, the two pegs 146 and 148 are inserted and retained in the two holes 135 and 137 respectively. The alternative assemblies of the detachable mounting mechanism may also includes two small flanges 152 and 154, having folded portions 156 and 158 respectively, attached on the front ends 112 and 122 of the first and second elongated arms 110 and 120 respectively, for preventing the deformable circular cutting ring 140 from rotating about the diameter 133, and for preventing the deformable circular cutting ring 140 from staying compressed. The difference between this alternative embodiment and the other embodiment is merely interchanging the locations of the pegs and holes.

The diameter of the deformable circular cutting ring may vary, depending on the requirement of the cataract surgeries performed. For example only, one of the various diameters may be five millimeters (5mm). The deformable circular cutting ring 130 may be a little thicker than the two clamp portions 116 and 126 of the first and second elongated arms 110 and 120, such that its sharp bottom circular cutting edge 132 is exposed, so that when cutting the incision on the anterior lens capsule, the two clamp portions 116 and 126 of the first and second elongated arms 110 and 120 will not interfere. The two clamp portions 116 and 126 of the first and second elongated arms 110 and 120 may be further curved to accommodate the circular circumferential configuration of the deformable circular cutting ring 130.

When the deformable circular cutting ring 130 is supported by the two front ends 112 and 122 of the first and second elongated arms 110 and 120 in the manner described above, it can be compressed into a narrow elliptical shape by simply squeezing the two handle portions 118 and 128 of the first and second elongated arms 110 and 120 inwardly toward each other. In a balanced position, however, the distance between the two front ends 112 and 122 of the first and second elongated arms 110 and 120 should be kept at about the same as the diameter 134 of the deformable circular cutting ring 130, so that the deformable circular cutting ring 130 is neither compressed nor stretched and remains in its original circular shape. A biasing mechanism is therefore provided for keeping the two elongated arms 110 and 120 in the balanced position. The biasing mechanism may include two thin and narrow spring plates 162 and 164. The first ends of the two thin and narrow spring plates 162 and 164 are respectively attached to the handle portions 118 and 128 of the first and second elongated arms 110 and 120, preferably very close or at the rear ends 114 and 124 of the first and second elongated arms 110 and 120. The second ends of the two thin and narrow spring plates 162 and 164 are hingeably attached at a hinging joint 166. In a preferred embodiment, the first thin spring plate 162 is integrally formed with the handle portion 118 of the first elongated arm 110 and extends from the rear end 114 of the first elongated arm 110, and the second thin spring plate 164 is integrally formed with the handle portion 128 of the second elongated arm 120 and extends from the rear end 124 of the second elongated arm 120.

The novel anterior capsular incising method of the present invention utilizes the unique deformable circular cutting ring 130. Referring to FIGS. 8 through 11, there is shown directions for use of the present invention anterior capsular incising apparatus 100 for cutting an adequate sized incision 12 on the anterior lens capsule 14 of an eye, through a narrow wound 16 cut on the corneoscleral tissue 18 of the eye.

As discussed above, before an incision 12 can be cut on the anterior lens capsule 14 of an eye for removing the natural intraocular lens of the eye and implanting an artificial intraocular lens therein, a small wound 16 must be cut on the corneoscleral tissue 18 of the eye to gain access to the anterior chamber of the eye, which anterior chamber is shown in FIGS. 8 through 11 by the space between the anterior lens capsule 14 and the corneoscleral tissue 18. It is preferable to have a small and narrow corneoscleral wound 16, typically not more than four millimeters (4mm) in width. However, the size of the anterior capsular incision 12 needs to be no less than five millimeters (5mm). The present invention solves this problem by utilizing the novel deformable circular cutting ring 130.

Figure 8:
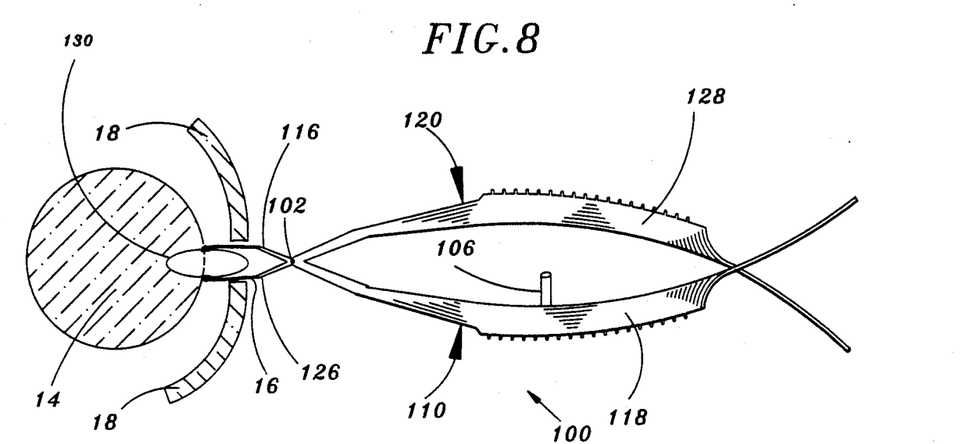
FIG. 8 is a top plan view showing the forward portion of the present invention anterior capsular incising apparatus compressed into a narrow configuration, so it can be inserted into the anterior chamber of an eye through a narrow wound cut on the corneoscleral tissue of the eye.

The first step of the present invention anterior capsular incising method is to detachably mount a fresh deformable circular, cutting ring 130 onto and between the clamp portions 116 and 126 of the first and second elongated arms 110 of the present invention anterior capsular incising apparatus 100 in the manner described earlier. The deformable circular cutting ring 130 and the two clamp portions 116 and 126 define a forward portion of the anterior capsular incising apparatus 100. To insert this forward portion into the anterior chamber of the eye through the narrow corneoscleral wound 16, the two handle portions 118 and 128 of the first and second elongated arms 110 and 120 are squeezed to compress the deformable circular cutting ring 130 into a narrow elliptical shape, so that the entire combination of the forward portion is kept in a very narrow and thin profile.

Figure 9:
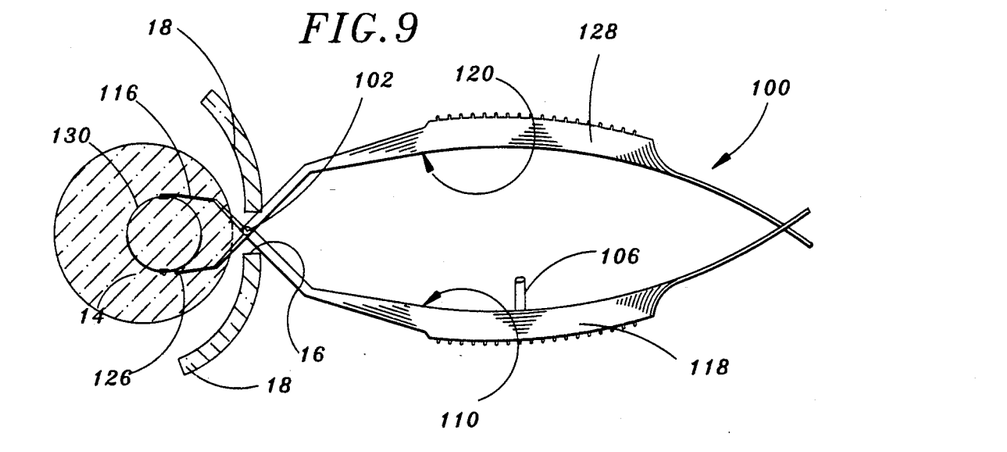
FIG. 9 is a top plan view showing once inside the anterior chamber of the eye, the forward portion of the present invention anterior capsular incising apparatus is allowed to return to its full configuration for cutting an incision on the anterior lens capsule and the crisscross axis at the arms is positioned at the location of the wound.

While the forward portion of the anterior capsular incising apparatus 100 is kept in the very narrow and thin profile, it is inserted into the anterior chamber of the eye through the narrow corneoscleral wound 16, until the crisscross joint 102 of the anterior capsular incising apparatus 100 is located at or adjacent to the narrow corneoscleral wound 16. Once the forward portion is inside the anterior chamber of the eye, the two handle portions 118 and 128 of the first and second elongated arms 110 and 120 are released, so that the deformable circular cutting ring 130 can return to its original full circular shape. Since the crisscross joint 102 of the anterior capsular incising apparatus 100 is located at the narrow corneoscleral wound 16, the widening of the two clamp portions 116 and 126 does not require a wider wound.

As the deformable circular cutting ring 130 is accurately located above the anterior lens capsule 14 of the eye, a downward force is applied on the deformable circular cutting ring 130 through the first and second elongated arms 110 and 120 to cut the incision 12 that has an adequate size, typically about five millimeters (5mm) in diameter. This cutting process is done while keeping the crisscross joint 102 of the anterior capsular incising apparatus 100 at or adjacent the narrow corneoscleral wound 102, so that the downward swing of the two clamp portions 116 and 126 again does not require a wider wound.

Figure 11:
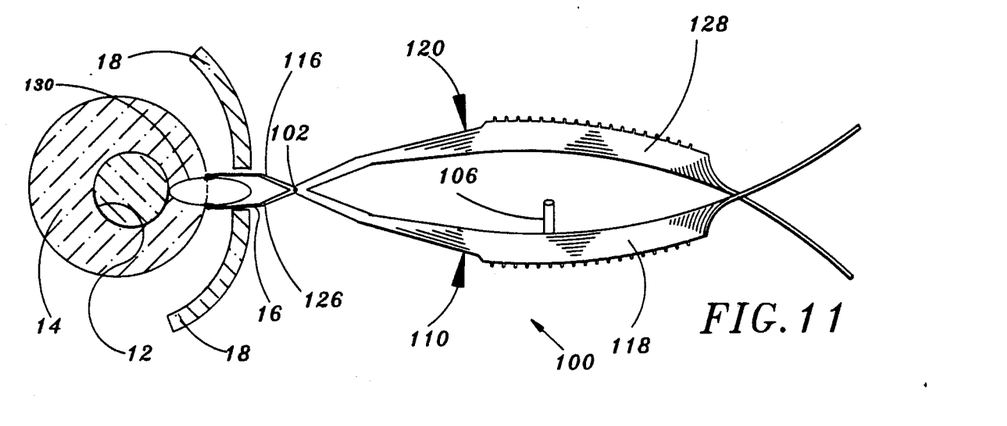
FIG. 11 is a top plan view showing after the anterior capsular incision is cut, the forward portion of the present invention anterior capsular incising apparatus is compressed again into the narrow configuration, so it can be withdrawn from the anterior chamber of the eye through the narrow corneoscleral wound.

After the incision 12 is made, the two handle portions 118 and 128 of the first and second elongated arms 110 and 120 are squeezed again to compress the deformable circular cutting ring 130 into the narrow elliptical shape, so that the forward portion of the anterior capsular incising apparatus 100 is again in the narrow and thin profile, and can be withdrawn from the anterior chamber through the narrow corneoscleral wound 16. The used deformable circular cutting ring 130 can be detached from the clamp portions 116 and 126 of the first and second elongated arms 110 and 120, so that it can be sharpened, sterilized or disposed of.

Defined in detail, the present invention is an anterior capsular incising apparatus, comprising: (a) a first elongated arm having a front end, a rear end, a clamp portion adjacent to its front end, and a handle portion adjacent to its rear end; (b) a second elongated arm having a front end, a rear end, a clamp portion adjacent to its front end, and a handle portion adjacent to its rear end; (c) means for hingeably attaching the first and second elongated arms at a crisscross joint between their the clamp portions and the handle portions, where the first and second elongated arms crisscross over each other; (d) a deformable circular cutting ring having a sharp bottom circular cutting edge; (e) means for detachably mounting the deformable circular cutting ring onto and between the clamp portions of the first and second elongated arms at two opposite ends of a diameter of the deformable circular cutting ring, such that the deformable circular cutting ring can be compressed into a narrow elliptical shape by squeezing the handle portions of the first and second elongated arms; (f) means for preventing the deformable circular cutting ring from rotating about the diameter of the deformable circular cutting ring; and (g) means for biasing the handle portions of the first and second elongated arms in a balanced position, such that the distance between the clamp portions of the first and second elongated arms are about the same as the diameter of the deformable circular cutting ring, so that when the handle portions of the first and second elongated arms are not squeezed, the deformable circular cutting ring is neither compressed nor stretched.

In one of the preferred embodiments of the present invention defined in detail: (a) the anterior capsular incising apparatus as defined above has means for hingeably attaching the first and second elongated arms at a crisscross joint between their the clamp portions and the handle portions which include a small mounting pin; (b) the means for detachably mounting the deformable circular cutting ring onto and between the clamp portions of the first and second elongated arms at two opposite ends of a diameter of the deformable circular cutting ring includes two small mounting pegs each integrally formed at one of the two opposite ends of the diameter of the deformable circular cutting ring, and two small mounting holes each located respectively at one of the two clamp portions of the first and second elongated arms, such that when the deformable circular cutting ring is mounted on the clamp portions of the first and second elongated arms, the two small mounting pegs are inserted and retained in the two small mounting holes respectively; or (c) the means for detachably mounting the deformable circular cutting ring onto and between the clamp portions of the first and second elongated arms at two opposite ends of a diameter of the deformable circular cutting ring includes two small mounting holes each located at one of the two opposite ends of the diameter of the deformable circular cutting ring, and two small mounting pegs each integrally, formed respectively at one of the two clamp portions of the first and second elongated arms, such that when the deformable circular cutting ring is mounted on the clamp portions of the first and second elongated arms, the two small mounting pegs are inserted and retained in the two small mounting holes respectively; (d) the means for preventing the deformable circular cutting ring from rotating about the diameter of the deformable circular cutting ring including two small flanges respectively attached to the two clamp portions of the two elongated arms, each small flange being located adjacent to one of the two opposite ends of the diameter of the deformable circular cutting ring; (e) the two small flanges each further has a folded portion for preventing the deformable circular cutting ring from staying compressed, such that the deformable circular cutting ring may be pulled back to its original shape by separating the two elongated arms; (f) the deformable circular cutting ring is detachably mounted at the front ends of the first and second elongated arms; (g) the means for biasing the handle portions of the first and second elongated arms in a balanced position including two thin spring plates each having a first end and a second end, where the first ends of the two thin spring plates are respectively attached to the handle portions of the first and second elongated arms, and the second ends of the two thin spring plates are hingeably attached to each other; (h) the first ends of the two thin spring plates are respectively attached to the rear ends of the first and second elongated arms; and (i) one of the two thin spring plates is integrally constructed with and extended from the rear end of the first elongated arms, and the other one of the two thin spring plates is integrally constructed with and extended from the rear end of the second elongated arms.

Defined also in detail, the present invention is an anterior capsular incising method of cutting an incision on the anterior lens capsule of an eye through a very narrow wound cut on the corneoscleral tissue of the eye, comprising: (a) detachably mounting a deformable circular cutting ring onto a pair of crisscrossing arms hinged at a crisscross joint and each having a forward portion and a rearward portion, such that the deformable circular cutting ring is disposed between the forward portions of the pair of crisscrossing arms and can be compressed into a narrow elliptical shape by squeezing the rearward portions of the pair of crisscrossing arms; (b) squeezing the rearward portions of the pair of crisscrossing arms to compress the deformable circular cutting ring into the narrow elliptical shape, and inserting the deformable circular cutting ring and the forward portions of the pair of crisscrossing arms into the anterior chamber of the eye through the narrow wound on the corneoscleral tissue while keeping the deformable circular cutting ring in the narrow elliptical shape, until the crisscross joint of the pair of crisscrossing arms is located at or adjacent to the narrow wound on the corneoscleral tissue; (c) releasing the rearward portions of the pair of crisscrossing arms so that the deformable circular cutting ring returns to its original full circular shape and applying a downward force on the deformable circular cutting ring to cut an incision on the anterior lens capsule of the eye; and (d) squeezing the rearward portions of the pair of crisscrossing arms again to compress the deformable circular cutting ring into the narrow elliptical shape, and withdrawing the deformable circular cutting ring and the forward portions of the pair of crisscrossing arms from the anterior chamber of the eye through the narrow wound on the corneoscleral tissue of the eye.

Defined broadly, the present invention is an anterior capsular incising apparatus, comprising: (a) a pair of crisscrossing arms hinged at a crisscross joint and each having a forward portion and a rearward portion; (b) a deformable circular cutting ring having a sharp bottom circular cutting edge; and (c) means for detachably mounting the deformable circular cutting ring onto and between the forward portions of the pair of crisscross arms at two spaced apart points of the deformable circular cutting ring, such that the deformable circular cutting ring can be compressed into a narrow elliptical shape by squeezing the rearward portions of the pair of crisscrossing arms.

Defined more broadly, the present invention is an anterior capsular incising apparatus comprising a deformable cutting member, which can be compressed into a narrow configuration for passing through a narrow wound cut on the corneoscleral tissue of an eye, and fully return to its original configuration once inside the anterior chamber of the eye, for cutting an incision on the anterior lens capsule of the eye.

Defined also more broadly, the present invention is an anterior capsular incising method utilizing a deformable cutting member, which can be compressed into a narrow configuration for passing through a narrow wound cut on the corneoscleral tissue of an eye, and fully return to its original configuration once inside the anterior chamber of the eye, for cutting an incision on the anterior lens capsule of the eye through a very narrow wound cut on the corneoscleral tissue.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing full public disclosure of at least one of its forms. However, such detailed description is not intended in any way to limit the broad features or principles of the present invention or the scope of patent monopoly to be granted.

What is claimed is:

1. An anterior capsular incising apparatus, comprising:
   a. a first elongated arm having a front end, a rear end, a clamp portion adjacent to its front end, and a handle portion adjacent to its rear end;
   b. a second elongated arm having a front end, a rear end, a clamp portion adjacent to its front end, and a handle portion adjacent to its rear end;
   c. means for hingeably attaching said first and second elongated arms at a crisscross joint between their said clamp portions and said handle portions, where said first and second elongated arms crisscross over each other;
   d. a deformable circular cutting ring having a sharp bottom circular cutting edge;
   e. means for detachably mounting said deformable circular cutting ring onto and between said clamp portions of said first and second elongated arms at two opposite ends of a diameter of said deformable circular cutting ring, such that said deformable circular cutting ring can be compressed into a narrow elliptical shape by squeezing said handle portions of said first and second elongated arms;
   f. means for preventing said deformable circular cutting ring from rotating about said diameter of said deformable circular cutting ring; and
   g. means for biasing said handle portions of said first and second elongated arms in a balanced position, such that the distance between said clamp portions of said first and second elongated arms are about the same as said diameter of said deformable circular cutting ring, so that when said handle portions of said first and second elongated arms are not squeezed, said deformable circular cutting ring is neither compressed nor stretched.

2. The anterior capsular incising apparatus as defined in claim 1 wherein said means for hingeably attaching said first and second elongated arms at a crisscross joint between their said clamp portions and said handle portions include a small mounting pin.

3. The anterior capsular incising apparatus as defined in claim 1 wherein said means for detachably mounting said deformable circular cutting ring onto and between said clamp portions of said first and second elongated arms at two opposite ends of a diameter of said deformable circular cutting ring includes two small mounting pegs each integrally formed at one of the two opposite ends of said diameter of said deformable circular cutting ring, and two small mounting holes each located at one of the two said clamp portions of said first and second elongated arms, such that when said deformable circular cutting ring is mounted on said clamp portions of said first and second elongated arms, the two small mounting pegs are inserted and retained in the two small mounting holes respectively.

4. The anterior capsular incising apparatus as defined in claim 1 wherein said means for detachably mounting said deformable circular cutting ring onto and between said clamp portions of said first and second elongated arms at two opposite ends of a diameter of said deformable circular cutting ring includes two small mounting holes each located at one of the two opposite ends of said diameter of said deformable circular cutting ring, and two small mounting pegs each integrally formed at one of the two said clamp portions of said first and second elongated arms, such that when said deformable circular cutting ring is mounted on said clamp portions of said first and second elongated arms, the two small mounting pegs are inserted and retained in the two small mounting holes respectively.

5. The anterior capsular incising apparatus as defined in claim 1 wherein said means for preventing said deformable circular cutting ring from rotating about said diameter of said deformable circular cutting ring comprises two small flanges respectively attached to said two clamp portions of said two elongated arms, each small flange being located adjacent to one of the two opposite ends of said diameter of said deformable circular cutting ring at the edge remote from said sharp bottom circular cutting edge.

6. The anterior capsular incising apparatus as defined in claim 5 wherein said two small flanges each further has a folded portion for preventing said deformable circular cutting ring from staying compressed, such that said deformable circular cutting ring may be pulled back to its original shape by separating said two elongated arms.

7. The anterior capsular incising apparatus as defined in claim 1 wherein said deformable circular cutting ring is detachably mounted at the front ends of said first and second elongated arms.

8. The anterior capsular incising apparatus as defined in claim 1 wherein said means for biasing said handle portions of said first and second elongated arms in a balanced position include two thin spring plates each having a first end and a second end, where the first ends of the two thin spring plates are respectively attached to the handle portions of said first and second elongated arms, and the second ends of the two thin spring plates are hingeably attached to each other.

9. The anterior capsular incising apparatus as defined in claim 8 wherein the first ends of said two thin spring plates are respectively attached to the rear ends of said first and second elongated arms.

10. The anterior capsular incising apparatus as defined in claim 9 wherein one of said two thin spring plates is integrally constructed with and extended from the rear end of said first elongated arm, and the other one of said two thin spring plates is integrally constructed with and extended from the rear end of said second elongated arm.

11. An anterior capsular incising apparatus, comprising:
 a. a pair of crisscrossing arms hinged at a crisscross joint and each having a forward portion and a rearward portion;
 b. a deformable circular cutting ring having a sharp bottom circular cutting edge; and
 c. means for detachably mounting said deformable circular cutting ring onto and between said forward portions of said pair of crisscrossing arms at two spaced apart points of said deformable circular cutting ring, such that said deformable circular cutting ring can be compressed into a narrow elliptical shape by squeezing said rearward portions of said pair of crisscrossing arms.

12. The anterior capsular incising apparatus as defined in claim 11 wherein said pair of crisscrossing arms are hingeably attached at said crisscross joint by a small pin.

13. The anterior capsular incising apparatus as defined in claim 11 wherein said means for detachably mounting said deformable circular cutting ring onto and between said forward portions of said pair of crisscrossing arms at two spaced apart points of said deformable circular cutting ring includes two small mounting pegs each integrally formed at one of the two spaced apart points of said diameter of said deformable circular cutting ring, and two small mounting holes each located at one of the two said forward portions of said pair of crisscrossing arms, such that when said deformable circular cutting ring is mounted on said forward portions of said pair of crisscrossing arms, the two small mounting pegs are inserted and retained in the two small mounting holes respectively.

14. The anterior capsular incising apparatus as defined in claim 11 wherein said means for detachably mounting said deformable circular cutting ring onto and between said forward portions of said pair of crisscrossing arms at two spaced apart points of said deformable circular cutting ring includes two small mounting holes each located at one of the two spaced apart points of said diameter of said deformable circular cutting ring, and two small mounting pegs each integrally formed at one of the two said forward portions of said pair of crisscrossing arms, such that when said deformable circular cutting ring is mounted on said forward portions of said pair of crisscrossing arms, the two small mounting pegs are inserted and retained in the two small mounting holes respectively.

15. The anterior capsular incising apparatus as defined in claim 11 further comprising means for preventing said deformable circular cutting ring from rotating about the axis defined by said two spaced apart locations of said deformable circular cutting ring.

16. The anterior capsular incising apparatus as defined in claim 15 wherein said means for preventing said deformable circular cutting ring from rotating about the axis defined by said two spaced apart locations of said deformable circular cutting ring includes two small flanges respectively attached to said two forward portions of said two crisscrossing arms, each small flange being located adjacent to one of the two spaced apart locations of said deformable circular cutting ring at the edge remote from said sharp bottom circular cutting edge.

17. The anterior capsular incising apparatus as defined in claim 16 wherein said two small flanges each further comprises a folded portion for preventing said deformable circular cutting ring from staying compressed, such that said deformable circular cutting ring may be pulled back to its original shape by separating said two crisscrossing arms.

18. The anterior capsular incising apparatus as defined in claim 11 further comprising means for biasing said pair of crisscrossing arms in a balanced position, such that when said rearward portions of said pair of crisscrossing arms are not squeezed, said deformable circular cutting ring is neither compressed nor stretched.

19. An anterior capsular incising apparatus comprising a deformable cutting member, which can be compressed into a narrow configuration for passing through a narrow wound cut on the corneoscleral tissue of an eye, and fully return to its original configuration once inside the anterior chamber of the eye, for cutting an incision on the anterior lens capsule of the eye.

20. The anterior capsular incising apparatus as defined in claim 19 further comprising a pair of crisscrossing arms hinged at a crisscross joint and each having a forward portion and a rearward portion, such that said deformable cutting member is disposed between the forward portions of the pair of crisscrossing arms and can be compressed into said narrow configuration by squeezing the rearward portions of the pair of crisscrossing arms.

21. An anterior capsular incising method of cutting an incision on the anterior lens capsule of an eye through a very narrow wound cut on the corneoscleral tissue of the eye, comprising;
   a. detachably mounting a deformable circular cutting ring onto a pair of crisscrossing arms hinged at a crisscross joint and each having a forward portion and a rearward portion, such that the deformable circular cutting ring is disposed between the forward portions of the pair of crisscrossing arms and can be compressed into a narrow elliptical shape by squeezing the rearward portions of the pair of crisscrossing arms;
   b. squeezing said rearward portions of said pair of crisscrossing arms to compress said deformable circular cutting ring into said narrow elliptical shape, and inserting said deformable circular cutting ring and said forward portions of said pair of crisscrossing arms into the anterior chamber of the eye through the narrow wound on the corneoscleral tissue while keeping said deformable circular cutting ring in said narrow elliptical shape, until said crisscross joint of said pair of crisscrossing arms is located at or adjacent to the narrow wound on the corneoscleral tissue;
   c. releasing said rearward portions of said pair of crisscrossing arms so that said deformable circular cutting ring returns to its original full circular shape, and applying a downward force on said deformable circular cutting ring to cut an incision on the anterior lens capsule of the eye; and
   d. squeezing said rearward portions of said pair of crisscrossing arms again to compress said deformable circular cutting ring into the narrow elliptical shape, and withdrawing said deformable circular cutting ring and said forward portions of said pair of crisscrossing arms from the anterior chamber of the eye through the narrow wound on the corneoscleral tissue of the eye.

22. The anterior capsular incising method as defined in claim 21 further comprising detaching said deformable circular cutting ring from said forward portions of said pair of crisscrossing arms after each use and disposing said deformable circular cutting ring.

23. An anterior capsular incising method utilizing a deformable cutting member, which can be compressed into a narrow configuration for passing through a narrow wound cut on the corneoscleral tissue of an eye, and fully return to its original configuration once inside the anterior chamber of the eye, for cutting an incision on the anterior lens capsule of the eye through a very narrow wound cut on the corneoscleral tissue.

24. The anterior capsular incising method as defined in claim 23 further comprising detachably mounting said deformable cutting member onto a pair of crisscrossing arms hinged at a crisscross joint and each having a forward portion and a rearward portion, such that said deformable cutting member is disposed between the forward portions of the pair of crisscrossing arms and can be compressed into said narrow configuration by squeezing the rearward portions of the pair of crisscrossing arms.

* * * * *